United States Patent [19]

Terada et al.

[11] Patent Number: 4,872,740
[45] Date of Patent: Oct. 10, 1989

[54] ENDOSCOPE

[75] Inventors: Hiromu Terada, Otake; Naoyuki Fukahori, Ayase; Kenichi Sakunaga, Otake, all of Japan

[73] Assignee: Mitsubishi Rayon Company, Ltd., Tokyo, Japan

[21] Appl. No.: 152,492

[22] Filed: Feb. 5, 1988

[30] Foreign Application Priority Data

Feb. 12, 1987 [JP] Japan .................................. 62-28092
Jun. 24, 1987 [JP] Japan .................................. 62-155297

[51] Int. Cl.$^4$ .................................................. G02B 6/06
[52] U.S. Cl. ...................................... 350/96.26; 128/7
[58] Field of Search ............... 350/96.24, 96.25, 96.26, 350/96.27, 96.28; 362/162; 128/4, 6, 7

[56] References Cited

U.S. PATENT DOCUMENTS

| | | | |
|---|---|---|---|
| 3,674,452 | 7/1972 | Strack | 65/4 |
| 4,523,806 | 6/1985 | Kojiha et al. | 350/96.25 |
| 4,618,884 | 10/1986 | Nagasaki | 350/96.26 X |
| 4,676,592 | 6/1987 | Nishioka et al. | 350/96.26 X |
| 4,721,359 | 1/1988 | Nishioka et al. | 350/96.26 |
| 4,736,734 | 4/1988 | Matsuura et al. | 350/96.26 X |
| 4,772,093 | 9/1988 | Abele et al. | 350/96.25 |

FOREIGN PATENT DOCUMENTS

| | | |
|---|---|---|
| 0026300 | 4/1981 | European Pat. Off. . |
| 0084216 | 7/1983 | European Pat. Off. . |
| 0136365 | 4/1985 | European Pat. Off. . |
| 3243302 | 9/1983 | Fed. Rep. of Germany . |

OTHER PUBLICATIONS

Laser+Elektro–Optik, vol. 9, No. 4, Nov. 1977, pp. 23-27; M. D. Reidenbach, "Eigenschaften von Kunststofflichtleitern".

Primary Examiner—William L. Sikes
Assistant Examiner—Akm E. Ullah
Attorney, Agent, or Firm—Oblon, Spivak, McClelland, Maier & Neustadt

[57] ABSTRACT

An endoscope comprising as an image-transmitting member a multifilament type plastic optical fiber, an object lens arranged on one end of the optical fiber and a device for guiding an image of an object transmitted to the other end of the optical fiber to an image-receiving portion, wherein the multifilament type plastic optical fiber has an islands-in-sea structure in which 50 to 10,000 light-transmitting core-sheath structure islands having a diameter of 5 to 200 μ are arranged in the sea so that the same positional relationship of the islands is maintained on both ends of the optical fiber, and the core occupancy ratio in the total cross-section of the optical fiber is at least 50%.

7 Claims, 3 Drawing Sheets

Fig. 5
Fig. 6
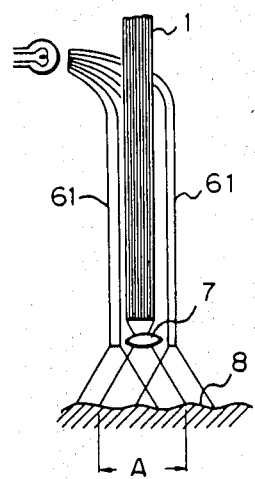
Fig. 7
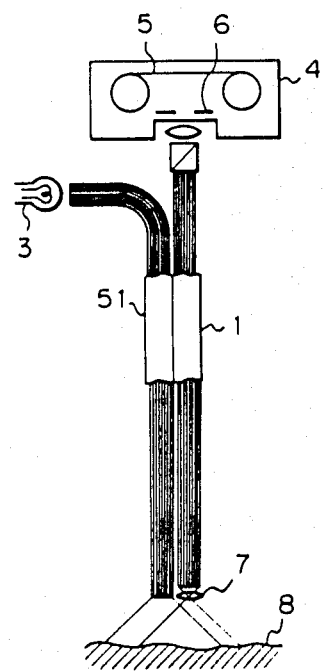
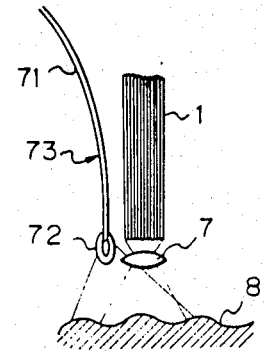

ENDOSCOPE

BACKGROUND OF THE INVENTION

(1) Field of the Invention

The present invention relates to a scope using a multifilament type plastic optical fiber as an image-transmitting member. More particularly, the present invention relates to an endoscope which makes it possible to observe an object in the dark field of vision as a bright and sharp image and shows a good handling property, such as an esophagoscope, a gastrocamera, an intestine endoscope, a bronchoscope, and endoscope exclusive for a specific organ, or a blood vessel endoscope.

(2) Description of the Related Art

A fiber scope comprising an image-transmitting member composed of an image-transmitting optical fiber bundle comprising a great number of bundled fine glass type optical filaments having a diameter of about 10 to about 50μ and a light-transmitting member composed of a plurality of optical filaments having a larger diameter, is known and disclosed in, for example, Japanese Unexamined Patent Publication No. 59-155231.

However, the known endoscope of this type is defective in the following points. Namely, the image-transmitting optical fiber bundle is formed by arranging several hundreds of quartz type optical filaments, which are very fine, rigid, and easily broken and have a poor handling property, so that the same positional relationship is maintained on both end faces of the image-transmitting optical fiber bundle, and therefore, it is very difficult to prepare this image-transmitting fiber bundle without breaking some of the fine quartz filaments, because of their poor handling property. Accordingly, the manufacturing cost is greatly increased. Furthermore, if even one of several hundreds of thus arranged quartz type optical filaments is broken, transmission of an image becomes impossible. Therefore, close attention should be paid when an endoscope is assembled by using this quartz type optical fiber and while the assembled endoscope is being used. When a break occurs, repair is very difficult and maintenance requires much labor. Moreover, the quartz type multifilament optical fiber bundle is rigid and has a poor handling property, and this poor handling property is a serious problem in case of a medical endoscope used for observing the interior of a fine tubule. Furthermore, this rigid optical fiber bundle causes pain to a patient during the observation. In order to improve the poor handling property and moderate the pain felt by a patient, the development of a material for a fiber scope having a good flexibility and softness is desired.

Still further, in the conventional endoscope fabricated by using the glass type optical fiber, the ratio of the area occupied by the core acting as a light-transmitting member in the cross-section of the optical fiber bundle is small, and the conventional endoscope is still unsatisfactory in that an object present in the dark field of vision cannot be observed as a bright and sharp image.

SUMMARY OF THE INVENTION

Under this background, research was made into the development of an endoscope capable of transmitting a sufficient quantity of light to the dark field of vision and producing a sharp transmitted image of an object present in the dark field of vision, substantially preventing breaking of an optical fiber upon assembly of the endoscope or during observation using the endoscope, and moderating the pain felt by a patient during observation, and as the result, it was found that these objects can be attained by using as the image-transmitting member a multifilament type plastic optical fiber having a specific structure comprising a number of arranged and integrated filaments. The present invention was completed based on this finding.

More specifically, in accordance with the present invention, there is provided an endoscope comprising as an image-transmitting member a multifilament type plastic optical fiber, an object lens arranged on one end of the multifilament type plastic optical fiber, and means for guiding an image of an object transmitted to the other end of the multifilament type plastic optical fiber to an image-receiving portion, wherein the multifilament type plastic optical fiber has an islands-in-sea structure in which 50 to 10,000 light-transmitting core-sheath structure islands having a diameter of 5 to 200μ are arranged in the sea so that the same positional relationship of the islands is maintained on both ends of the optical fiber, and the core occupancy ratio in the total cross-section of the optical fiber is at least 50%.

DESCRIPTION OF THE PREFERRED EMBODIMENTS

Figure 1:
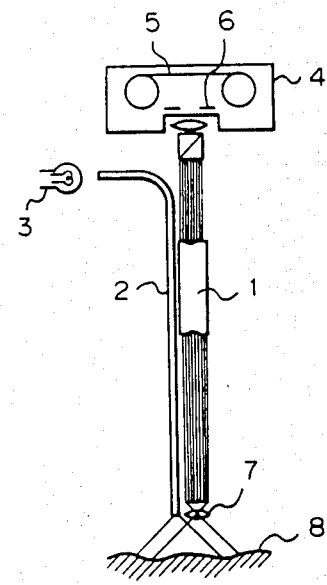
FIG. 1 is a schematic side view illustrating one embodiment of the endoscope of the present invention.

Referring to FIG. 1, which is a schematic diagram illustrating one embodiment of the endoscope of the present invention, this endoscope comprises a light source system for guiding illuminating light of an object 8 to be observed, from a light source 3, for example, a light-transmitting optical fiber 2 having a diameter of about 100 to 1000μ, an optical system for focusing an image of the object 8 on the top end of the multifilament optical fiber, for example, an object lens 7, and a multifilament type plastic optical fiber 1 for guiding the focused image precisely to an image-receiving portion, for example, a still camera 4. Note, in the still camera 4, reference numeral 5 represents a film and reference numeral 6 represents a shutter.

Figure 2:
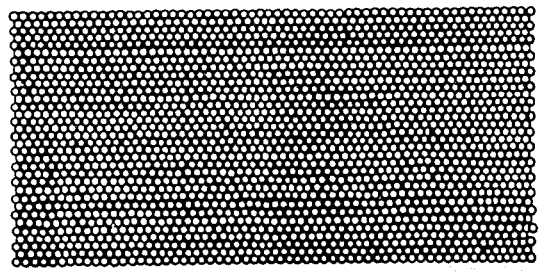
FIG. 2 is an enlarged microscope view showing the section of a multifilament type plastic optical fiber used as the image-transmitting member in the fiber scope of the present invention.
Figure 3:
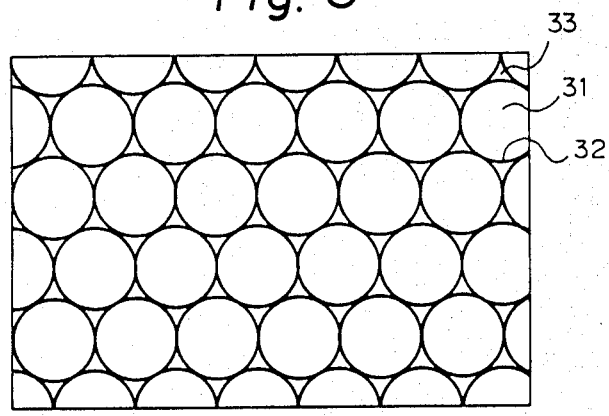
FIG. 3 is an enlarged electron microscope view showing a part of FIG. 2.

The most characteristics feature of the endoscope of the present invention resides in that a multifilament type plastic optical fiber having an excellent flexibility is used as the image-transmitting member. A multifilament type plastic optical fiber having 1363 islands arranged in a zigzag-stacked structure in the sea is shown as an example in the enlarged microscope sectional view of FIG. 2, and a part of this multifilament type optical fiber is shown in the enlarged electron microscope sectional view. In FIG. 3 31 represents an island, reference numeral 32 represents a sheath of the core (i.e., the island), and reference numeral 33 represents the sea.

In order to maintain a good image-transmitting property, preferably the light transmission loss is not increased. From this viewpoint, the section of each island should preferably have a substantially uniform hexagonal or more polygonal shape resembling a circular shape. In the present invention, preferably the light transmission loss of the multifilament type optical fiber is smaller than 3 dB/m, especially smaller than 1.5 dB/m.

The number of the islands arranged in the sea is in the range of from 50 to 10,000, and the core occupancy ratio in the total cross-section of the multifilament type optical fiber is at least 50%, preferably 70 to 95%. When a multifilament type plastic optical fiber in which the core occupancy ratio and the number of islands satisfy the above-mentioned requirements is used as the image-transmitting member, the quantity of transmitted light is greatly increased over the quantity of light transmitted by the conventional quartz optical fiber bundle heretofore used for the endoscope, and a sharp and bright image can be obtained.

The brightness index I defined by the following formula (1) is preferably adopted for evaluating the quantity of transmitted light or the image-transmitting property of the multifilament type plastic optical fiber used in the present invention:

$$I = S \cdot NA^2 \cdot 10^{-(\frac{\alpha L}{10})} \quad (1)$$

wherein S is the occupancy ratio of cores in the multifilament type optical fiber's cross-section, $\alpha$ is the transmission loss (dB/m) per meter of the multifilament type optical fiber, NA is the numerical aperture, and L is the length (m) of the used multifilament type optical fiber.

The brightness index I of the multifilament type plastic optical fiber of the present invention is preferably at least $4.5 \times 10^{-2}$, especially preferably at least $5 \times 10^{-2}$.

In order to obtain a multifilament plastic optical fiber having this brightness index, the occupancy ratio of the total core cross-section in the multifilament type optical fibers should be at least 50%, preferably at least 55%, especially preferably at least 60%.

The numerical aperture NA is defined by the following formula (2):

$$NA = \sqrt{n_1^2 - n_2^2} \quad (2)$$

wherein $n_1$ is the refractive index of the core-forming plastic material and $n_2$ is the refractive index of the sheath-forming plastic materials. In the present invention, preferably the difference between the refractive index $n_1$ of the core-forming polymer and the refractive index $n_2$ of the sheath-forming polymer in the islands is at least 0.015.

Preferably, the core-forming polymer having the refractive index $n_1$ and the sheath-forming polymer having the refractive index $n_2$ is selected so that the numerical aperture NA defined by the formula (2) is at least 0.16, especially at least 0.3. Where the NA value is at least 0.16, a multifilament type optical fiber having a brightness index of at least $4.5 \times 10^{-3}$ can be effectively prepared.

In order to maintain a good sharpness and brightness in the transferred image, it is generally preferred that L is smaller than 10.

In order to obtain a transferred image having a good resolution, preferably the diameter of the islands constituting the multifilament type optical fiber is 5 to 100$\mu$.

If the multifilament type plastic optical fiber acting as the image-transmitting member of the endoscope of the present invention has an image transfer characteristic such that, when a converging lens and a light-receiving face are disposed on both ends of the multifilament type optical fiber and a test pattern of a resolving power test target (USAF 1951) is transmitted by white light according to the method of USAF 1951, the resolving power is at least 2 line pairs/mm where each line pair consists of one white line and one black line, a sharp and bright image can be transferred.

Furthermore, the multifilament type plastic optical fiber used in the present invention is characterized in that the optical fiber can transfer a sharp image even in the state where the optical fiber is wound on a rod having a diameter of 10 mm by 3 to 20 turns. The endoscope of the present invention comprising this multifilament type optical fiber as the image-transmitting member is advantageous in that the image-transmitting member is not broken, the handling property is good, and the pain felt by a patient is greatly moderated.

As examples of the plastics for forming the core, sheath and sea components of the multifilament type optical fiber used in the present invention, there can be selected from polymethyl methacrylate (n=1.49), copolymers (n=1.47 to 1.50) composed mainly of methyl methacrylate, polystyrene (n=1.58), copolymers (n=1.50 to 1.58) composed mainly of styrene, styrene/acrylonitrile copolymers (n=1.56), poly-4-methylpentene-1 (n=1.46), ethylene/vinyl acetate copolymers (n=1.46 to 1.50), a polycarbonate (n=1.50 to 1.57), polychlorostyrene (n=1.61), polyvinylidene chloride (n=1.63), polyvinyl acetate (n=1.47), methyl methacrylate/styrene, vinyltoluene or $\alpha$-methylstyrene/maleic anhydride terpolymers or quadripolymers (n=1.50 to 1.58), polydimethylsiloxane (n=1.40), polyacetal (n=1.48), polytetrafluoroethylene (n=1.35), polyvinylidene fluoride (n=1.42), polytrifluoroethylene (n=1.40), polyperfluoropropylene (n=1.34), fluoroethylene copolymers or terpolymers (n=1.35 to 1.40), polyvinylidene fluoride/polymethyl methacrylate blends (n=1.42 to 1.46), copolymers composed mainly of a fluoromethacrylate represented by the general formula $CH_2=C(CH_3)COORf$ in which Rf stands for $(CH_2)_n(CF_2)_nH$ (n=1.37 to 1.42), $(CH_2)_m(CF_2)_nF$ (n=1.37 to 1.40), $CH-(CF_3)_2$ (n=1.38), $C(CF_3)_3$ (n=1.36), $CH_2CF_2CHFCF_3$ (n=1.40) or $CH_2CF(CF_3)_2$ (n=1.37), copolymers of these fluoromethacrylates (n=1.36 to 1.40), copolymers of such a fluoromethacrylate with methyl methacrylate (n=1.37 to 1.43), polymers composed mainly of a fluoroacrylate represented by the general formula $CH_2=CH \cdot COOR'f$ in which R'f stands for $(CH_2)_m(CF_2)_nF$ (n=1.37 to 1.40), $(CH_2)_m(CF_2)_nH$ (n=1.37 to 1.41), $CH_2CF_2CHFCF_3$ (n=1.41) or $CH(CH_3)_2$ (n=1.38), copolymers of these fluoroacrylate (n=1.36 to 1.41), copolymers of such a fluoroacrylate and a fluoromethacrylate as described above (n=1.36 to 1.41), copolymers of these fluoroacrylate and fluoromethacrylate and methyl methacrylate (n=1.37 to 1.43), homopolymers and copolymers (n=1.37 to 1.42) composed mainly of a 2-fluoroacrylate represented by the general formula $CH_2=CF \cdot COOR''f$ in which $R''f$ stands for $CH_3$, $(CH_2)_m(CF_2)_nF$, $(CH_2)_m(CF_2)_nH$, $CH_2CF_2CHFCF_3$ or $C(CF_3)_2$ and fluorine-containing alkyl fumaric acid ester polymers (n=1.30 to 1.42).

The multifilament type plastic optical fiber used as the image-transmitting member of the endoscope of the present invention can be effectively prepared, for example, according to the process disclosed in Japanese Patent Application No. 60-142985.

Figure 4:
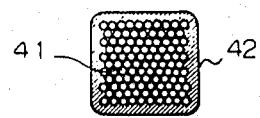
FIG. 4 is a sectional view illustrating a multifilament type plastic optical fiber having a black covering layer formed on the periphery thereof; and, FIGS. 5, 6, and 7 are views showing parts of the endoscope of the present invention provided with a means for illuminating an object to be observed.

If a black covering layer 42 is formed on the periphery of the multifilament type plastic optical fiber 41 used as the image-transmitting member of the endoscope of the present invention as shown in FIG. 4, a transmission of unnecessary miscellaneous information can be prevented, and a sharper and brighter image can be transmitted. The black covering layer can be formed covering a composition comprising carbon black, lead oxide or other black organic pigment and polyethylene, polyvinyl chloride, polymethyl methacrylate or a fluorine type polymer on the multifilament type optical fiber by using an extrusion die or the like. Although the multifilament type plastic optical fiber as shown in FIG. 4 has a substantially rectangular cross-section, the fiber may have a cross-section of another shape, such as of circular or non-circular.

As the method for illuminating an object to be observed in the endoscope of the present invention, a method can be adopted in which a light guide 2 composed of a multifilament type plastic optical fiber comprising filaments having a diameter of about 100 to about 1000μ is arranged on the periphery of the image-transmitting multifilament type plastic optical fiber 1, as shown in FIG. 5. Another method can be adopted in which a light guide 61 composed of a plurality of optical fibers having a diameter of about 200 to 1000μ is arranged on the periphery of the image-transmitting multifilament type plastic optical fibers as shown in FIG. 6. Further, a light guide 73 composed of an electric wire cable 71 and a microlamp 72 may be used as shown in FIG. 7.

In the endoscope shown in FIG. 5, a multifilament type plastic optical fiber is used as the light guide 51 for guiding light from the light source 3 to the object 8 to be observed.

Furthermore, a method may be adopted in which an appropriate number of light-transmitting optical fibers 61 is uniformly arranged on the periphery of the image-transmitting multifilament type optical fiber 1, as shown in FIG. 6. In the endoscope shown in FIG. 6, the observation range A of the image-transmitting multifilament type optical fiber 1 can be uniformly illuminated. In this embodiment, preferably at least 4, especially about 8 to about 30, of plastic optical fiber having a diameter of 100 to 500μ, especially at least 200μ, are uniformly arranged as the light-transmitting optical fibers 61 on the image-transmitting multifilament type plastic optical fiber. The image-transmitting multifilament optical fiber 1 shown in FIG. 6 may have the periphery thereof covered with a black covering layer as shown in FIG. 4, and in this endoscope, a very sharp and bright image can be transmitted. Note, if not only the image-transmitting multifilament type plastic optical fiber 1 but also the light-transmitting optical fibers 61 arranged on the periphery thereof are covered with a black covering layer, the cable can be integrated and smoothly inserted into the interior of a living body. In this case, it is preferable to use a biocompatible polymer, such as polyethylene, a fluorine-containing polymer, a polyurethane or a vinyl acetate/ethylene copolymer, as the covering material.

The present invention will now be described in detail with reference to the following examples, that by no means limit the scope of the invention.

EXAMPLE 1

Multifilament plastic optical fibers having the characteristics shown in Table 1 were obtained by carrying out conjugate spinning by using an apparatus having a structure shown in Japanese Patent Application No. 60-142985 and a spinneret having 1350 holes, polymethyl methacrylate having a refractive index $n_1$ of 1.492 as the core-forming polymer, a fluoromethylacrylate polymer having a refractive index $n_2$ of 1.415 as the sea-forming polymer, and a vinylidene fluoride copolymer having a refractive index of 1.40 as the sheath-forming polymer.

TABLE 1

| | Run No. | | | | |
|---|---|---|---|---|---|
| | 1 | 2 | 3 | 4 | 5 |
| Outer diameter | 0.3 mm × 0.6 mm | 0.55 mm × 1.1 mm | 0.73 mm × 1.46 mm | 1.3 mm × 2.6 mm | 2.0 mm × 4.0 mm |
| Core diameter (μ) | 10 | 20 | 20 | 50 | 80 |
| NA | 0.51 | 0.51 | 0.51 | 0.51 | 0.51 |
| $n_1-n_2$ | 0.092 | 0.092 | 0.092 | 0.092 | 0.092 |
| Core occupancy ratio (%) | 60 | 69 | 40 | 75 | 80 |
| Transmission loss (dB/m) | 1.3 | 1.1 | 1.1 | 1.0 | 0.85 |
| Length (m) of multifilament type optical fiber | 2 | 3 | 3 | 5 | 5 |
| Brightness index of multifilament type optical fiber | $7.2 \times 10^{-2}$ | $7.1 \times 10^{-2}$ | $4.1 \times 10^{-2}$ | $5.2 \times 10^{-2}$ | $6.6 \times 10^{-2}$ |
| Resolving power (line pairs/mm) of multifilament type optical fiber | 25.39 group 4 element 5 | 14.3 group 3 element 6 | 14.3 group 3 element 6 | 4.49 group 2 element 2 | 2.24 group 1 element 2 |
| Image-transmitting property when optical fiber was wound on rod having diameter of 10 mm by n turns | 3 turns good | good | good | good | good |
| | 10 turns good | good | good | good | fair |

Each of the so-obtained multifilament type plastic fibers was integrated as the image-transmitting optical fiber with 10 polymethyl methacrylate plastic optical fibers having a diameter of 100μ as the fiber for guiding light from the light source, and an object lens and an eye lens were attached to fabricate an endoscope having a structure shown in FIG. 1. A very sharp and light image was obtained in the endoscope.

When a repeated bending test was carried out, none of the optical fibers was broken, and each optical fiber had a very good handling property.

as the sheath-forming polymer and vinylidene fluoride polymer having a refractive index of 1.40 as the sea-forming polymer.

TABLE 2

| | Run No. | | |
|---|---|---|---|
| | 6 | 7 | 8 |
| Outer diameter | 0.46 mm × 0.92 mm | 0.33 mm × 0.66 mm | 0.24 mm × 0.48 mm |
| Core diameter ($\mu$) | 10 | 7 | 5 |
| NA | 0.53 | 0.53 | 0.53 |
| $n_1-n_2$ | 0.097 | 0.097 | 0.097 |
| Core occupancy ratio (%) | 55 | 53 | 51 |
| Transmission loss (dB/m) | 1.6 | 1.8 | 2.0 |
| Fiber length (m) | 2 | 2 | 2 |
| Brightness index | $7.4 \times 10^{-2}$ | $6.5 \times 10^{-2}$ | $5.6 \times 10^{-2}$ |

EXAMPLE 2

Two of the multifilament type plastic optical fibers prepared at run No. 1 of Example 1 shown in Table 1 were doubled and the periphery was covered with a polyethylene resin blackened by carbon black in a thickness of about 100$\mu$. Then, 12 plastic optical fibers having a diameter of 250$\mu$ were uniformly arranged on the black covering layer, and a protecting layer of a vinyl acetate/ethylene copolymer was formed on the periphery and an endoscope as shown in FIG. 6 was fabricated. It was confirmed that the resolving power was high and the endoscope could transmit a very bright image.

EXAMPLE 3

Two of the multifilament type plastic optical fibers prepared at run No. 2 of Example 1 shown in Table 1 were combined to fabricate an endoscope having a structure as shown in FIG. 5, in which one optical fiber was used as the image-transmitting member and the other optical fiber was used as the light guide. It was confirmed that a very bright and clear image was obtained in the endoscope.

When the repeated bending test was carried out, it was found that the optical fiber was not broken and the handling property was very good.

EXAMPLE 4

A square stacked structure was formed by using 20 of the multifilament type plastic optical fibers prepared at run No. 1 of Example 1, and 8 of polymethyl methacrylate type optical fibers having a diameter of 250$\mu$ were arranged on the periphery of the square stacked multifilament type optical fibers and an endoscope having a structure as shown in FIG. 6 was fabricated. It was confirmed that a very sharp and bright image was obtained in the endoscope.

When the repeated bending test was conducted, it was found that none of the optical fibers was broken, and the handling property was very good.

EXAMPLE 5

Multifilament type plastic optical fibers having characteristics shown in Table 2 were obtained by carrying out conjugate spinning by using the same apparatus as used in Example 1 and a spinneret having 2990 holes, polymethyl methacrylate having a refractive index of 1.492 as the core-forming polymer, a perfluoroalkyl methacrylate polymer having a refractive index of 1.395

Three endoscopes having a structure shown in FIG. 7 were fabricated by using 10 each of the multifilament type plastic optical fibers obtained at the respective run Nos. 6, 7, and 8 and electric lamps as the light source. In each endoscope, a very sharp and bright image was obtained.

When the repeated bending test was carried out, it was found that none of the optical fibers was broken, and the handling property was very good.

We claim:

1. An endoscope comprising:
    an image-transmitting member made of a multifilament type plastic optical fiber having a substantial rectangular cross-section,
    an object lens arranged on one end of the optical fiber and means for guiding an image of an object transmitted to the other end of the multifilament type optical fiber to an image-receiving portion, wherein said multifilament type plastic optical fiber has an islands-in-sea structure in which 50 to 10,000 light-transmitting core-sheath structure islands having a substantially circular cross-section with a diameter of 5 to 200$\mu$, arranged in the sea such that the same positional relationship of the islands is maintained on both ends of the multifilament type optical fiber, and the core occupancy ratio in the total cross-section of the multifilament type optical fiber is at least 50%.

2. An endoscope as set forth in claim 1, wherein the periphery of the multifilament type plastic optical fiber as the image-transmitting member is covered with a black covering layer.

3. An endoscope as set forth in claim 1, wherein the multifilament type plastic optical fiber as the image-transmitting member has an image transfer characteristic such that, when an object lens and an image-receiving face are disposed on both the ends of the multifilament type plastic optical fiber and a test pattern of a resolving power test target (USAF 1951) is transmitted by white light, the resolving power of said structure is at least 2 line pairs/mm where each line pair is defined as one white line and one black line of said test target.

4. An endoscope as set forth in claim 3, wherein the multifilament type plastic optical fiber as the image-transmitting has an image transfer characteristic, and even if the multifilament type plastic optical fiber is wound on a rod having a diameter of 10 mm by at least 3 turns, the image transfer characteristic is not degraded.

5. An endoscope as set forth in claim 1, wherein as a means for illuminating an object to be observed, a plurality of light-transmitting optical fibers having a diameter of 100 to 1000μ is arranged on the periphery of the image-transmitting multifilament type plastic optical fiber, one end thereof being located at the vicinity of the object lens and the other end thereof being located at a light source.

6. An endoscope as set forth in claim 1, wherein as a means for illuminating an object to be observed, a multifilament type plastic optical fiber is arranged, into one end of which light from a light source is introduced.

7. An endoscope set forth in claim 1, wherein as a means for illuminating an object to be observed, a plurality of light guides consisting an electric wire cable and a microlamp are arranged on the periphery of the image-transmitting multifilament type plastic optical fiber, one end thereof being located at the vicinity of the object lens and the other end thereof being located at an electric source.

* * * * *